United States Patent [19]

Watanabe et al.

[11] Patent Number: 5,608,131

[45] Date of Patent: Mar. 4, 1997

[54] PENTACYCLIC HYDROCARBON COMPOUND AND HALOGENATED PENTACYCLIC HYDROCARBON COMPOUND, AND PREPARATION PROCESSES THEREOF

[75] Inventors: Yoshihisa Watanabe, Joyo; Takeaki Mitsudo, Nishigyo-ku; Shi-Wei Zhang, Toyonaka, all of Japan

[73] Assignee: Maruzen Petrochemical Co., Ltd., Tokyo, Japan

[21] Appl. No.: 375,292

[22] Filed: Jan. 20, 1995

[30] Foreign Application Priority Data

Jan. 25, 1994 [JP] Japan ......................................... 6-6133

[51] Int. Cl.⁶ ............................ C07C 403/00; C07C 2/76; C07C 13/28
[52] U.S. Cl. ............................................. 585/362; 585/360
[58] Field of Search ...................................... 585/360, 362

[56] References Cited

U.S. PATENT DOCUMENTS

| | | | |
|---|---|---|---|
| 3,329,732 | 7/1967 | Bastian et al. | 585/362 |
| 4,031,150 | 6/1977 | Suld et al. | 585/362 |
| 4,208,355 | 6/1980 | Myers, Jr. et al. | 585/362 |
| 4,222,800 | 9/1980 | Myers, Jr. et al. | 585/360 |
| 4,229,612 | 10/1980 | Hall, Jr. et al. | 585/360 |
| 4,275,254 | 6/1981 | Schneider et al. | 585/360 |

OTHER PUBLICATIONS

P. Eaton et al., "The Peristylane System", J. Am. Chem. Soc., vol. 94, No. 3, pp. 1014–1016.

P. Eaton et al., "Synthesis of Peristylane and the acs–(Cs)–C14–Tetraquinane, C14–Pentaquinane, and Nor-peristylane Systems", J. Am. Chem. Soc., vol. 99, No. 8, pp. 2751–2766.

T. Mitsudo et al., "Ruthenium Complex–catalysed Dimerization of Norbornadiene to Pentacyclotetradecadiene", J. Chem. Soc., Chem. Commun., pp. 435–436.

Primary Examiner—Glenn A. Caldarola
Assistant Examiner—J. Pasterczyk
Attorney, Agent, or Firm—Oblon, Spivak, McClelland, Maier & Neustadt, P.C.

[57] ABSTRACT

A process for the preparation of the compound of the formula

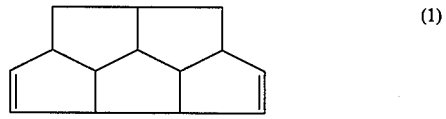

(1)

comprising dimerizing norbornadiene in the presence of N-methylpiperidine and a combined catalyst of (1,5-cyclooctadiene)(1,3,5-cyclooctatriene)-ruthenium and N,N-dimethylacrylamide.

2 Claims, No Drawings

PENTACYCLIC HYDROCARBON COMPOUND AND HALOGENATED PENTACYCLIC HYDROCARBON COMPOUND, AND PREPARATION PROCESSES THEREOF

BACKGROUND OF THE INVENTION

1. Field of the Invention

The present invention relates to a pentacyclic hydrocarbon compound (hereinafter called "hydrocarbon compound") useful as a fuel for rocket and jet engines, or as a monomer for polymerization, a halogenated pentacyclic hydrocarbon compound (hereinafter called "halogenated hydrocarbon compound") which is obtained by halogenation of the above hydrocarbon compound and useful as a raw material for perfume bases and the like, and preparation processes thereof.

2. Description of the Background Art

Acetylene obtained by cracking of naphtha has heretofore been effectively used as a raw material for products of the so-called acetylene chemical industry, such as vinyl chloride, vinyl acetate and chloroprene. Cyclopentadiene similarly obtained by cracking of naphtha has also been effectively used as a raw material for synthetic rubber and resins and a raw material for synthesizing camphor and derivatives thereof, and alkaloids according to the Diels-Alder reaction.

The above-described acetylene and cyclopentadiene are also used as raw materials for synthesizing norbornadiene. It has been known that a large amount of norbornadiene can be synthesized with ease from acetylene and cyclopentadiene by the Diels-Alder reaction. However, there has been a demand for development of a method of making a more fruitful use of acetylene and cyclopentadiene, in its turn, a method of making a fruitful use of norbornadiene.

SUMMARY OF THE INVENTION

It is thus an object of the present invention to provide a method of making a fruitful use of norbornadiene, namely, to provide novel compounds which are derived from norbornadiene and can be used in various fields, and preparation processes thereof.

With the foregoing circumstances in view, the present inventors have carried out an extensive investigation. As a result, it has been found that when norbornadiene is reacted in the presence of a specific catalyst, it is dimerized to synthesize a novel hydrocarbon compound, i.e., pentacyclo[$5.4.2^{1.7}.1^{3.6}.0^{10.13}.0^{12.14}$]tetradeca-4,8-diene, that the hydrocarbon compound is halogenated with ease, and that the hydrocarbon compound and a halide thereof, i.e., pentacyclo[$5.4.2^{1.7}.1^{3.6}.0^{10.13}.0^{12.14}$]-4,5,8,9-tetrahalogenotetradecane can be used for various purposes, thus leading to completion of the present invention.

In an aspect of the present invention, there is thus provided a hydrocarbon compound represented by the following formula (1):

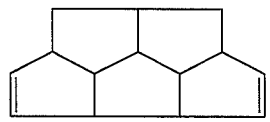
(1)

In another aspect of the present invention, there is also provided a halogenated hydrocarbon compound represented by the following formula (2):

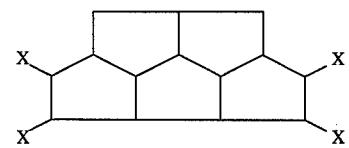
(2)

wherein X means a halogen atom.

In a further aspect of the present invention, there is provided a process for the preparation of a hydrocarbon compound represented by the following formula (1):

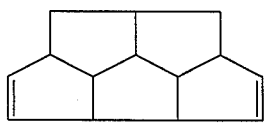
(1)

which comprises dimerizing norbornadiene in the presence of a combined catalyst of a ruthenium complex and an N,N-dialkyl(meth)acrylamide.

In a still further aspect of the present invention, there is provided a process for the preparation of a halogenated hydrocarbon compound represented by the following formula (2):

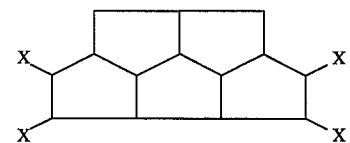
(2)

wherein X means a halogen atom, which comprises halogenating a hydrocarbon compound represented by the following formula (1):

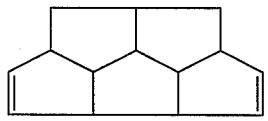
(1)

The hydrocarbon compound according to the present invention can be effectively used as a jet-propulsion fuel for rocket and jet engines either as it is or in the form of a hydrogenated product, or as a monomer for polymerization or an intermediate for preparation of various derivatives. Since the hydrocarbon compound according to the present invention is obtained by using, as a raw material, norbornadiene synthesized from acetylene and cyclopentadiene which are provided in plenty by cracking of naphtha, the fruitful use of acetylene and cyclopentadiene can be achieved. The halogenated hydrocarbon compound obtained by halogenating the hydrocarbon compound is useful as a raw material for perfume bases when halogen atoms thereof are substituted by hydroxyl groups.

The above and other objects, features and advantages of the present invention will be readily appreciated as the same becomes better understood from the preferred embodiments of the present invention, which will be described subsequently in detail, and from the appended claims.

DETAILED DESCRIPTION OF THE PREFERRED EMBODIMENTS

The compounds (1) and (2) according to the present invention are prepared in accordance with, for example, the following reaction scheme:

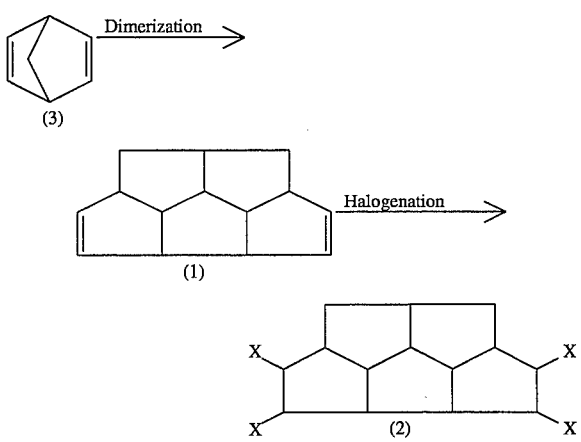

wherein X has the same meaning as defined above.

More specifically, norbornadiene (3) is dimerized in the presence of a combined catalyst of a ruthenium complex and an N,N-dialkyl(meth)acrylamide, thereby resulting in the formulation of the hydrocarbon compound (1) according to the present invention. Besides, the halogenated hydrocarbon compound (2) is prepared by halogenating the hydrocarbon compound (1).

Norbornadiene (3) used as a raw material for the hydrocarbon compound represented by the formula (1) in the present invention is prepared with ease, for example, by the Diels-Alder reaction using, as raw materials, acetylene obtained by cracking of naphtha, and cyclopentadiene obtained similarly.

Examples of the ruthenium complex as one component of the catalyst used for the dimerization of norbornadiene (3) in the present invention include ruthenium-unsaturated hydrocarbon complexes, ruthenium carbonyl compounds, ruthenium-phosphine complexes, ruthenium-carbonyl phosphine complexes and the like. Specific preferable examples thereof include (1,5-cyclooctadiene)(1,3,5-cyclooctatriene)ruthenium and dihydridocarbonyl tris(triphenylphosphine)ruthenium. The amount of the ruthenium complex to be used is preferably 0.025–25 mols, in particular, 0.5–5 mols, per 100 mols of norbornadiene as the raw material.

As examples of the N,N-dialkyl(meth)acrylamide, there may be preferably used those whose alkyl moieties have 1–8 carbon atoms, in particular, 1–3 carbon atoms. Of these, those containing a methyl group, ethyl group, propyl group or isopropyl group are particularly preferred. The amounts of such N,N-dialkyl(meth)acrylamides to be used are preferably 1–100 mols, in particular, 5–50 mols, per mol of the ruthenium complex.

In order to prevent the dimerization of the N,N-dialkyl(meth)acrylamide, a tertiary amine may be added as a stabilizer for the catalyst in the present invention. Examples of the tertiary amine include N-alkylpiperidines whose alkyl moiety has 1-8 carbon atoms and trialkylamines.

Since the tertiary amine serves not only as the stabilizer for the catalyst, but also as a solvent, no particular limitation is imposed on its amount to be used. In the compound (2) according to the present invention, the halogen atoms as the substituents include a bromine atom, fluorine atom, chlorine atom and iodine atom.

The dimerization of norbornadiene (3) is conducted by adding the tertiary amine to the catalyst as needed, and reacting norbornadiene in the presence of this catalyst. In this case, the reaction may be desirably performed in an atmosphere of an inert gas such as argon gas or nitrogen gas.

Upon the reaction, a solvent may or may not be used. If used, no particular limitation is imposed on the kind of the solvent. The reaction may be conducted at a temperature of 10°–200° C., preferably 50+– 150° C. for 0.5–20 hours, preferably 2–12 hours.

The thus-obtained hydrocarbon compound (pentacyclo[5.4.2$^{1.7}$.1$^{3.6}$.0$^{10.13}$.0$^{12.14}$]tetradeca-4,8-diene) represented by the formula (1) has a compact structure in which five 5-membered rings are condensed, and is high in density per unit volume. Therefore, this compound is effectively used as a jet-propulsion fuel for rocket and jet engines either as it is or in the form of a hydrogenated product. Since the compound has two independent double bonds, it is useful as a monomer for various polymerization reactions such as radical polymerization, cationic polymerization and anionic polymerization and may also be used in RIM (reaction injection molding) according to a metathesis reaction like cyclopentadiene (CPD). Further, its copolymer with ethylene may be used as a material for optical lenses. Furthermore, the reactivity of the double bonds contained therein can be put to good use to obtain various derivatives by halogenation, epoxidation or the like. Therefore, the hydrocarbon compound is also useful as an intermediate for preparation of the various derivatives.

The preparation of the halogenated hydrocarbon compound of the formula (2) from the hydrocarbon compound of the formula (1) can be performed with ease by subjecting the hydrocarbon compound of the formula (1) to halogenation in accordance with a method known per se in the art. More specifically, the hydrocarbon compound of the formula (1) is dissolved in a solvent such as chloroform to give a concentration of preferably 0.01–5.0 mol/liter. A gas of a halogen such as bromine is blown into this solution. Alternatively, a solution of the halogen in a solvent such as chloroform is added dropwise to the above solution, whereby the halogenated hydrocarbon compound of the formula (2), in which two molecules of the halogen have been added to the double bonds in the hydrocarbon compound of the formula (1), can be obtained.

In this case, the solvent is not limited to chloroform, but any solvent may be used so far as it can dissolve the hydrocarbon compound of the formula (1) and the halogen. The reaction may be conducted at a temperature of –20° to 100° C., preferably 30° to 80° C.

The thus-obtained halogenated hydrocarbon compound (pentacyclo[5.4.2$^{1.7}$.1$^{3.6}$.0$^{10.13}$.0$^{12.14}$]-4,5,8,9-tetrahalogenotetradecane) represented by the formula (2) is useful as a raw material for perfume bases, and the like when the halogen atoms thereof are substituted by hydroxyl groups.

The present invention will hereinafter be described in detail by reference to the following examples. However, it should be borne in mind that this invention is not limited to these examples.

EXAMPLE 1

A 20-ml sealed glass tube containing a magnetic stir bar therein was charged with 0.46 g ( 5.0 mmol ) of norbornadiene, and 0.03 1 g ( 0.1 mmol ) of ( 1,5-cyclooctadiene) (1,3,5-cyclooctatriene) ruthenium and 0.10 ml (1.0 mmol) of N, N-dimethylacrylamide as a catalyst, and 0.30 ml (2.5 mmol) of N-methylpiperidine as a stabilizer for the catalyst in an argon gas atmosphere, and then subjected to a reaction at 80° C. for 10 hours. The resulting reaction product was treated twice by distillation under reduced pressure (by means of a Kugelrohr-type distillation apparatus), thereby obtaining 0.390 g ( yield: 85% ) of colorless crystals.

This compound had a melting point of 102°–104° C., and was found to be pentacyclo-[5.4.2$^{1.7}$.1$^{3.6}$.0$^{10.13}$.0$^{12.14}$]tetradeca-4,8-diene represented by the formula (1) from the following analyses.
Elementary analysis (wt. %): Found: C, 90.54; H, 8.73 Calculated: C, 91.26; H, 8.74.
MS (m/z): 184 (M$^+$).
$^1$H-NMR (CDCl$_3$, ppm):
δ=1.43(dt,2H,J=13.2,5.4 Hz),
δ=1.75(dt,2H,J=13.2,8.4 Hz),
δ=2.57(qt,1H,J=8.8,5.9 Hz),
δ=2.89 (m, 1H),
δ=3.05(m,2H),
δ=3.35(m,4H),
δ=5.34 (d, 2H,J=5.6 Hz),
δ=5.51(dd,2H,J=5.6,2.2 Hz).
IR Spectrum (KBr, cm$^{-1}$): 3043, 2934, 2902, 1451, 1349, 848, 723.

EXAMPLE 2

A reaction was conducted in the same manner as in Example 1 except that 0.23 g (2.5 mmol) of norbornadiene and 0.25 ml (2.5 mmol) of N,N-dimethylacrylamide were used, thereby obtaining 0.219 g (yield: 95%) of a compound similar to the compound of Example 1. The thus-obtained compound was analyzed in the same manner as in Example 1 and was found to be pentacyclo[5.4.2$^{1.7}$.1$^{3.6}$.0$^{10.13}$.0$^{12.14}$]tetradeca-4,8-diene.

EXAMPLE 3

A reaction was conducted in the same manner as in Example 1 except that 0.23 g (2.5 mmol) of norbornadiene and 0.025 ml (0.25 mmol) of N,N-dimethylacrylamide were used and the reaction was conducted for 8 hours, thereby obtaining 0.069 g (yield: 30%) of a compound similar to the compound of Example 1. The thus-obtained compound was analyzed in the same manner as in Example 1 and was found to be pentacyclo[5.4.2$^{1.7}$.1$^{3.6}$.0$^{10.13}$.0$^{12.14}$]tetradeca-4,8-diene.

COMPARATIVE EXAMPLE 1

A reaction was conducted under the same reaction conditions as in Example 1 except that acetylene and cyclopentadiene, which are both raw materials for norbornadiene, were used instead of norbornadiene to try a direct reaction of acetylene and cyclopentadiene. It was however impossible to obtain pentacyclo[5.4.2$^{1.7}$.1$^{3.6}$.0$^{10.13}$.0$^{12.14}$]tetradeca-4,8-diene.

EXAMPLE 4

A solution (concentration: 1 mol/liter) of bromine in chloroform was added dropwise to a solution of 0.18 g (1.00 mmol) of pentacyclo-[5.4.2$^{1.7}$.1$^{3.6}$.0$^{10.13}$.0$^{12.14}$]-tetradeca-4,8-diene obtained in Example 1 in 1 ml of chloroform while stirring the solution of this compound, and the drop addition was stopped at the time the brown color of the chloroform solution of bromine became free from vanishing. The stirring was continued further for 30 minutes to deposit white crystals. The white crystals were collected by filtration, washed with cold chloroform and dried, thereby obtaining colorless crystals.

This compound had a melting point of 232°–234° C., and was found to be pentacyclo-[5.4.2$^{1.7}$.1$^{3.6}$.0$^{10.13}$.0$^{12.14}$]-4,5,8,9-tetrabromotetradecane represented by the following formula (4) from the following analyses.

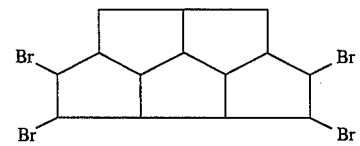

Elementary analysis (wt. % ): Found: C, 33.14; H, 3.06; Br, 63.21 Calculated: C, 33.37; H, 3.20; Br, 63.43.
$^1$H-NMR (CDCl$_3$, ppm):
δ=1.59(dt,2H,J=15.0,7.0 Hz),
δ=2.20(dt,2H,J=15.0,9.9 Hz),
δ=2.71(qt,1H,J=9.9,7.0 Hz),
δ=2.90 (m, 2H),
δ=3.18 (m, 4H),
δ=3.25(m, 1H),
δ=4.24(dm,2H,J=9.9 Hz),
δ=4.38(dd,2H,J=9.9,6.2 Hz).
IR Spectrum (KBr, cm$^{-1}$): 2963, 2939, 1456, 1312, 1285, 1229, 1202, 1183, 1165, 762, 743, 708.

What is claimed is:
1. A hydrocarbon compound represented by the following formula (1):

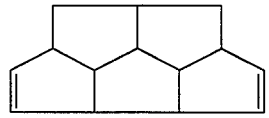

2. A process for the preparation of a hydrocarbon compound represented by the following formula (1):

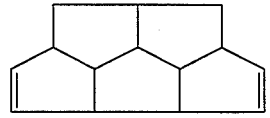

said process comprising dimerizing norbornadiene in the presence of N-methylpiperidine and a combined catalyst of (1,5-cyclooctadiene)(1,3,5-cyclooctatriene)-ruthenium and N,N-dimethylacrylamide.

* * * * *